US007540849B2

(12) United States Patent
Chang et al.

(10) Patent No.: US 7,540,849 B2
(45) Date of Patent: Jun. 2, 2009

(54) HINGE POSITIONING STRUCTURE

(75) Inventors: Yu-Kuang Chang, Taoyuan County (TW); Ching-Hung Chang, Taoyuan County (TW); Wen-Kuan Peng, Taoyuan County (TW)

(73) Assignee: Quanta Storage Inc., Guishan Shiang, Taoyuan County (TW)

( * ) Notice: Subject to any disclaimer, the term of this patent is extended or adjusted under 35 U.S.C. 154(b) by 183 days.

(21) Appl. No.: 11/549,121

(22) Filed: Oct. 13, 2006

(65) Prior Publication Data

US 2007/0129659 A1 Jun. 7, 2007

(30) Foreign Application Priority Data

Oct. 16, 2005 (TW) .............................. 94136431 A

(51) Int. Cl.
*A61F 5/00* (2006.01)

(52) U.S. Cl. ........................................... 602/16; 602/19

(58) Field of Classification Search ..................... 602/5, 602/16, 19; 285/406
See application file for complete search history.

(56) References Cited

U.S. PATENT DOCUMENTS 6,464,354 B1 * 10/2002 Chen et al. .................. 351/120
2006/0152005 A1 * 7/2006 Kertesz et al. .............. 285/406

* cited by examiner

*Primary Examiner*—Michael A. Brown
(74) *Attorney, Agent, or Firm*—Winston Hsu

(57) ABSTRACT

A hinge positioning structure is used to couple a body and a leg of a stand. The hinge positioning structure has a joint groove formed in the body, a stopper attached at the bottom of the joint groove having an elastic body with a spring strip, and a hinge formed in the leg positioned in the joint groove. The leg has two sides, each side having a pivot positioned according to a corresponding pivot hole in the joint groove for rotatable insertion into the corresponding pivot hole of the joint groove, and two flanges, each flange parallel to the spring strip and radially protruding a first height sufficient to contact with the spring strip for generating a resistance.

18 Claims, 5 Drawing Sheets

HINGE POSITIONING STRUCTURE

BACKGROUND OF THE INVENTION

1. Field of the Invention

The present invention relates to folding stands, and more particularly, to a folding stand that uses a hinge with a positioning groove to press against a spring strip.

2. Description of the Prior Art

A general foldable stand comprises a body and legs. When the legs are unfolded, the body stands with the legs. When the legs are folded, the stand becomes portable. Please refer to FIG. 1. FIG. 1 is a diagram illustrating a foldable stand of the prior art. As shown in FIG. 1, the foldable stand comprises a body 1 and a leg 3. The body 1 comprises a joint groove 2, a spring 5, a bolt 6, and a container 9. The leg 3 comprises a support 8 and a hinge 4. The hinge 4 comprises a set of positioning holes 7.

The joint groove 2 is disposed in the body 1 for accommodating the hinge 4. The spring 5 is disposed in the joint groove 2 to push the bolt 6. Thus, the bolt 6 is pushed into one hole of the set of positioning holes 7 when that hole moves to the appropriate position, and the leg 3 is fixed. The set of positioning holes 7 comprises a first hole and a second hole.

When the leg 3 is unfolded, the support 8 is moved away from the container 9 of the body 1. The support 8 rotates around the hinge 4 until the bolt 6 is pushed into the first hole of the set of positioning holes 7. Then the leg 3 is fixed at an unfolded position and a predetermined angle is formed between the leg 3 and the body 1. Thus, the foldable stand stands.

When the leg 3 is folded, the support 8 is moved toward the container 9 of the body 1. The support 8 rotates around the hinge 4 until the bolt 6 is pushed into the second hole of the set of positioning holes 7. Then the leg 3 is fixed at a folded position and the support 8 is contained in the container 9.

When a user folds the stand, the user has to apply a sufficient force to the support 8 to provide a torque that can enable the bolt 6 inserted into the first hole to slide out and to insert into the second hole. The same condition exists when the user unfolds the stand. Therefore, in design, the spring 5 is not too strong and the set of positioning holes 7 is not too deep. Utilizing such a design allows the user to apply only a little force to fold or unfold the stand, and prevents the bolt 6 from jamming in the positioning holes 7.

However, the design of the stand of the prior art is unable to provide a strong hold for the stand. The stand can fold and unfold too easily. That means the stand is not firm. When the stand is unfolded to carry a heavy object, the leg 3 may be folded by the pressure of the heavy object, causing the object to fall. Thus, the prior art cannot provide a strong stand for the user.

SUMMARY OF THE INVENTION

According to the present invention, a hinge positioning structure used to couple a body and a leg of a stand comprises a joint groove formed in the body comprising two sides, each side of the joint groove comprising a pivot hole, a stopper attached at the bottom of the joint groove having an elastic body comprising a spring strip, and a hinge formed in the leg positioned in the joint groove comprising two sides, each side having a pivot positioned according to the corresponding pivot hole for rotatable insertion into the corresponding pivot hole of the joint groove, and two flanges, each flange parallel to the spring strip and radially protruding a first height sufficient to contact with the spring strip for generating a resistance.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
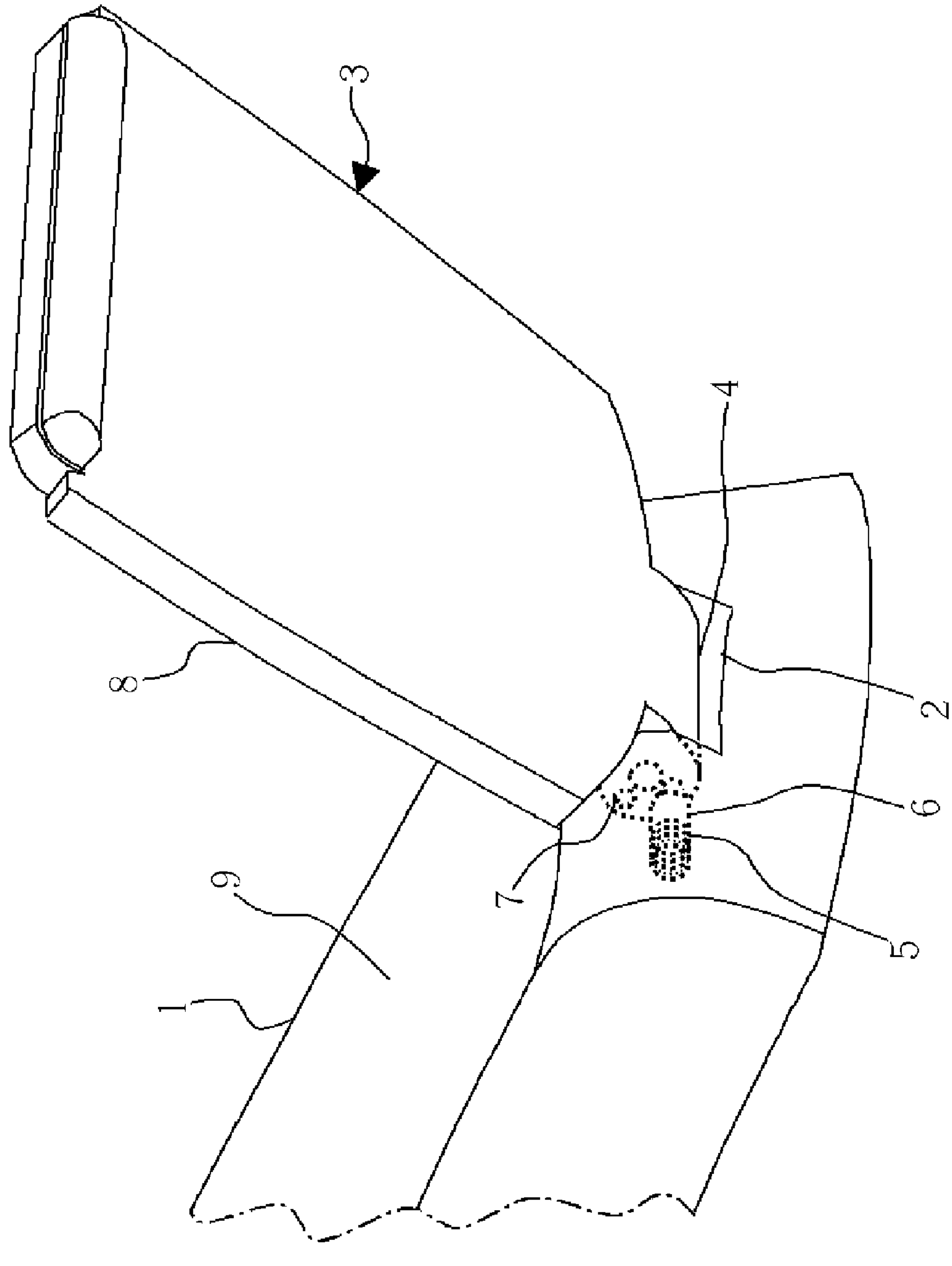
Fig. 1 Prior Art
FIG. 1 is a diagram of a stand according to the prior art.
Figure 2:
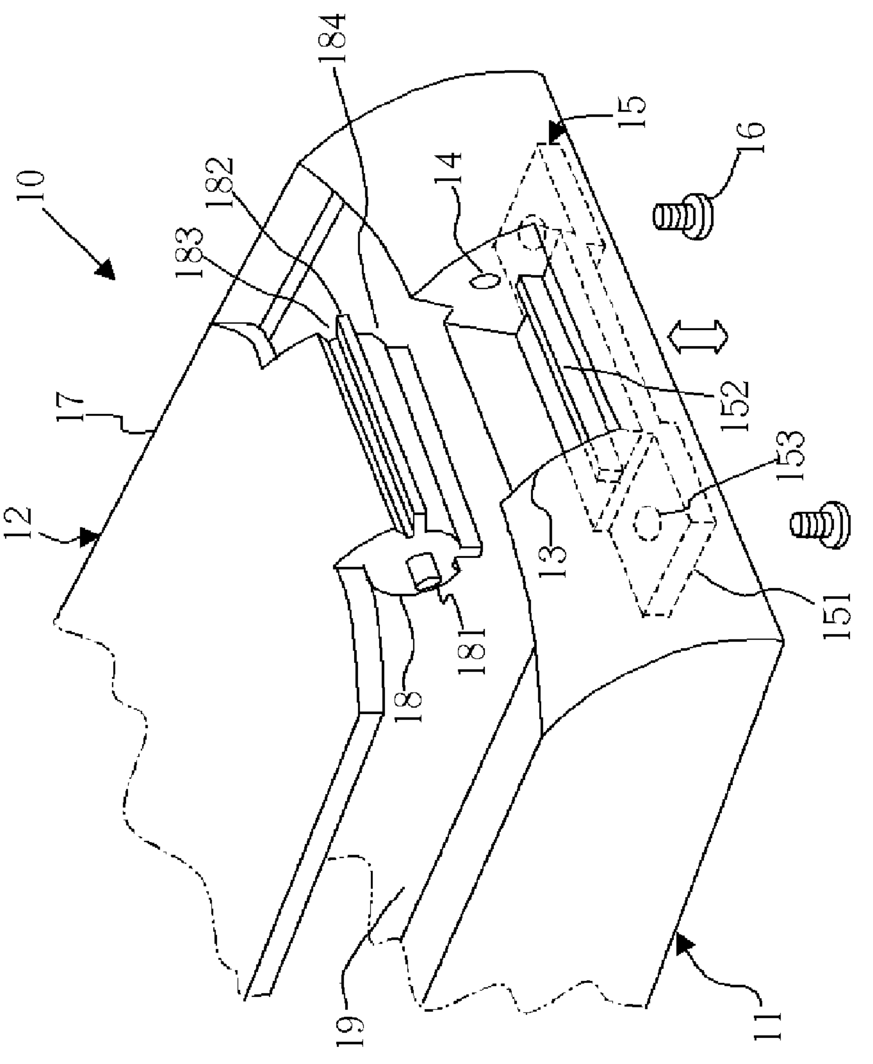
FIG. 2 is a diagram of a hinge positioning structure according to the present invention.

Please refer to FIG. 2. FIG. 2 is a diagram illustrating a stand using a hinge positioning structure 10 of the present invention. The stand comprises a body 11, a leg 12, and a hinge positioning structure 10. The hinge positioning structure 10 is used to couple the body 11 and the leg 12 for enabling the leg 12 to rotate relative to the body 11. Thus the stand is able to fold and unfold.

Please continue referring to FIG. 2. The body 11 of the present invention comprises a joint groove 13, a stopper 15, and a container 19. The joint groove 13 comprises two pivot holes 14 at both sides of the joint groove 13. The stopper 15 is disposed at the bottom of the joint groove 13 and is made of rubber or another elastic material. The stopper 15 comprises a baseboard 151 and a spring strip 152. The baseboard 151 comprises two thick sides and a protruding center to form a bridge-shaped board. Each of the two thick sides has a screw hole 153. The spring strip 152 is disposed on the protruding center and the position of the spring strip 152 slightly deviates from a central line of the protruding center. The shape of the spring strip 152 is a rectangular bar. The stopper 15 is attached below the joint groove 13 by screwing screws 16 into the screw hole 153 of each of the two sides of the baseboard 151. Thus, the protruding center is positioned at the bottom of the joint groove 13 so that the spring strip 152 is placed across the bottom of the joint groove 13 and protrudes to an appropriate height. Additionally, the stopper 15 is elastic to allow the protruding center to move downward within a space as shown by an arrow in FIG. 2.

Please continue referring to FIG. 2. The leg 12 of the present invention comprises a support 17 and a hinge 18. The support 17 is basically board-shaped. The hinge 18 is basically cylinder-shaped to match the joint groove 13. The hinge 18 comprises two pivots 181, two flanges 182, two positioning grooves 183, and a spacious groove 184. The two pivots 181 are disposed at both sides of the hinge 18 for insertion into the pivot holes 14 of the body 11. The sizes of the pivots 181 match those of the pivot holes 14. The flanges 182 are cuboids and protrude from the hinge 18 to a predetermined height to contact with the spring strip 152 when the hinge 18 rotates over a predetermined angle. One of the flanges 182 is disposed along the axis of the hinge 18 and positioned to contact with the spring strip 152 when the stand of the present invention is folded. The other one of the flanges 182 is disposed along the axis of the hinge 18 and positioned to contact with the spring strip 152 when the stand of the present invention is unfolded. Each of the positioning grooves 183 is disposed at the outer side of each of the flanges 182 and parallel to the flanges 182. The spacious groove 184 is disposed between the inner sides of the flanges 182.

Please continue referring to FIG. 2. The following describes assembly of the hinge positioning structure 10 of the present invention. The screws 16 are screwed through the screw holes 153 onto the body 11 for fixing the stopper 15 below the joint groove 13 and positioning the spring strip 152 across the bottom of the joint groove 13. Thus, the spring strip 152 protrudes a predetermined height from the bottom of the joint groove 13. The hinge 18 is installed with the pivots 181 embedded in the pivot holes 14 of the joint groove 13. After embedding in the pivot holes 14, the pivots 181 are still able to rotate. During the rotation of the hinge 18, the spacious groove 184 provides a predetermined angle to the hinge 18 to revolve without being blocked by the spring strip 152 because the spring strip 152 does not contact with the spacious groove 184. However, the positioning grooves 183 are narrow enough to hold the spring strip 152 such that the leg 12 cannot rotate.

Figure 3:
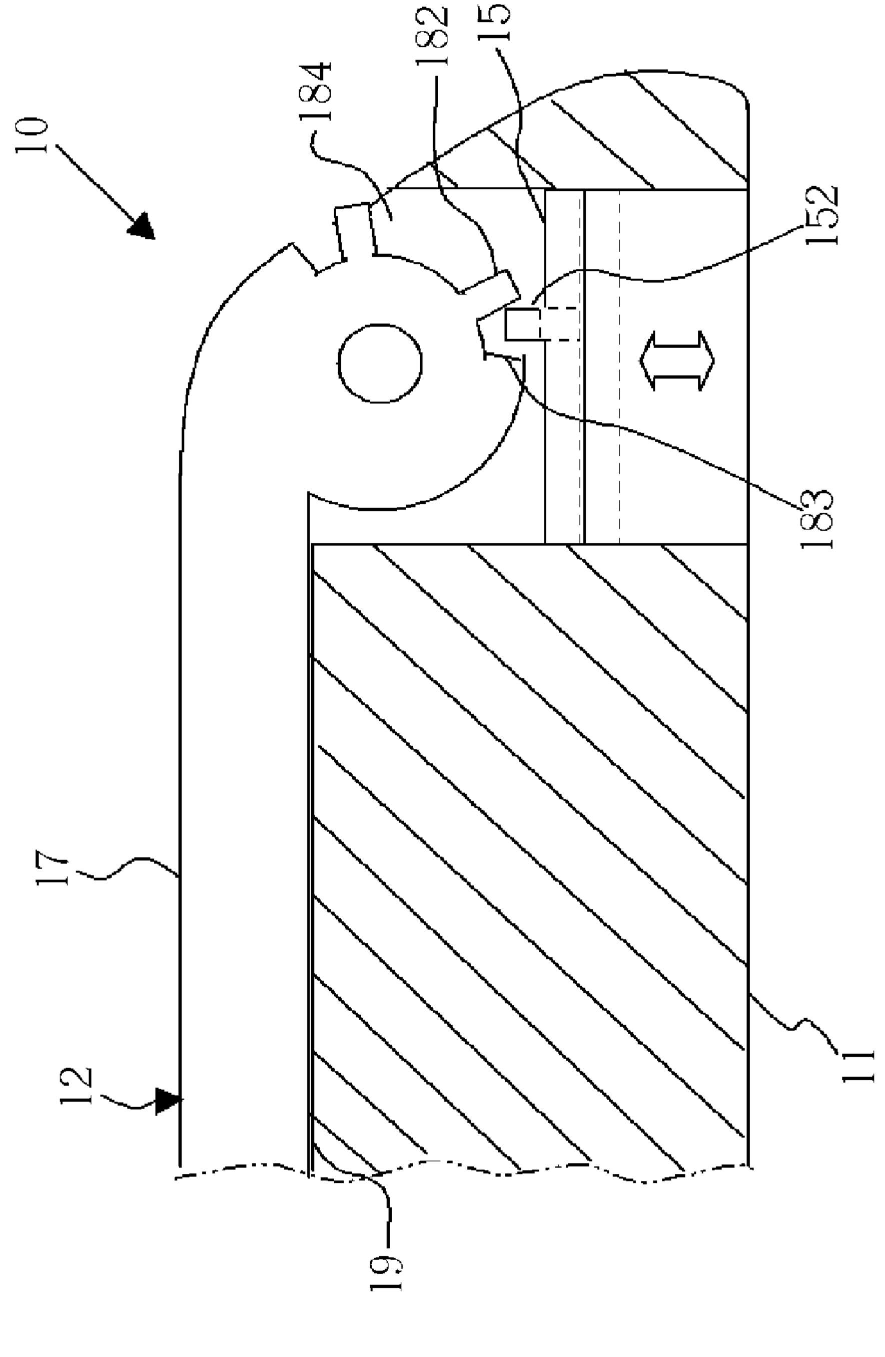
FIG. 3 is a diagram of compressing a spring strip in the hinge positioning structure of FIG. 2.

Please refer to FIG. 3. When the hinge positioning structure 10 is folded, the support 17 of the leg 12 is situated in the container 19 of the body 11, the spring strip 152 of the stopper 15 is stuck in the positioning groove 183, the spring strip 152 is restricted by the positioning groove 183, and the flange 182 obstructs the spring strip 152 to hold the support 17 to the body 11 for easier transport. When a force is applied to rotate the support 17, the flange 182 compresses the spring strip 152, such that the protruding center of the stopper 15 underneath the spring strip 152 will flex downward (as shown by the dotted lines in FIG. 3), such that the flange 182 can pass over the spring strip 152. When the spacious groove 184 is over the spring strip 152, the support 17 can rotate freely.

Figure 4:
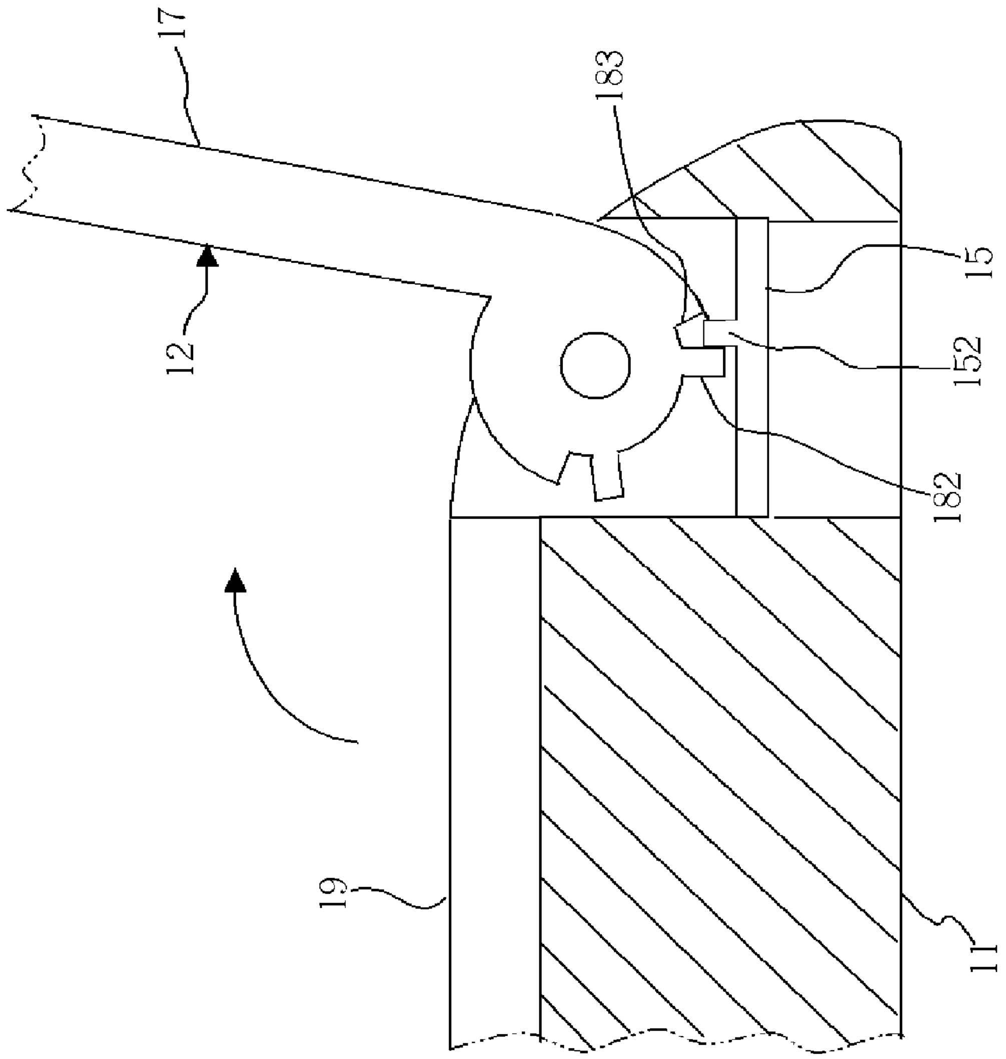
FIG. 4 is a diagram of unfolding a leg of the hinge positioning structure of FIG. 2.

Please refer to FIG. 4. When the support 17 rotates such that the flange 182 contacts the spring strip 152, a force is applied to rotate the support 17 again, and the flange compresses the spring strip 152, causing the protruding center of the stopper 15 underneath the spring strip 152 to flex downward, such that the flange 182 can pass over the spring strip 152. The spring strip 152 enters, and is restricted by, the positioning groove 183, such that the support 17 cannot rotate further, and holding the leg 12 in an unfolded state. Because the spring strip 152 is slightly offset from the center of the stopper, i.e. is not on the axis of the joint groove 13, the contact area of the length of the flange 182 and the length of the spring strip 152 can form an elongated surface which, aside from providing a stronger support to support a heavier weight in the body 11, can also prevent wear caused by the point support stress of the prior art. If the leg 12 is positioned on a plane, the body 11 can stand.

When the leg 12 is folded, an opposite sequence to that described above for unfolding occurs. As the support 17 is pressed toward the body 11, the flange 182 compresses the spring strip 182, such that the center portion of the stopper 15 flexes downward to allow the flange 182 to pass. As the support 17 continues toward the body 11, the spring strip 182 passes freely through the spacious groove 184 until the flange 182 is contacted. The flange 182 compresses the spring strip 182, such that the center portion of the stopper 15 flexes downward to allow the flange 182 to pass. The spring strip 182 enters, and is restricted by, the positioning groove 183, and the support 17 is held firmly against the body 11 in the container 19, which completes folding of the leg 12.

Figure 5:
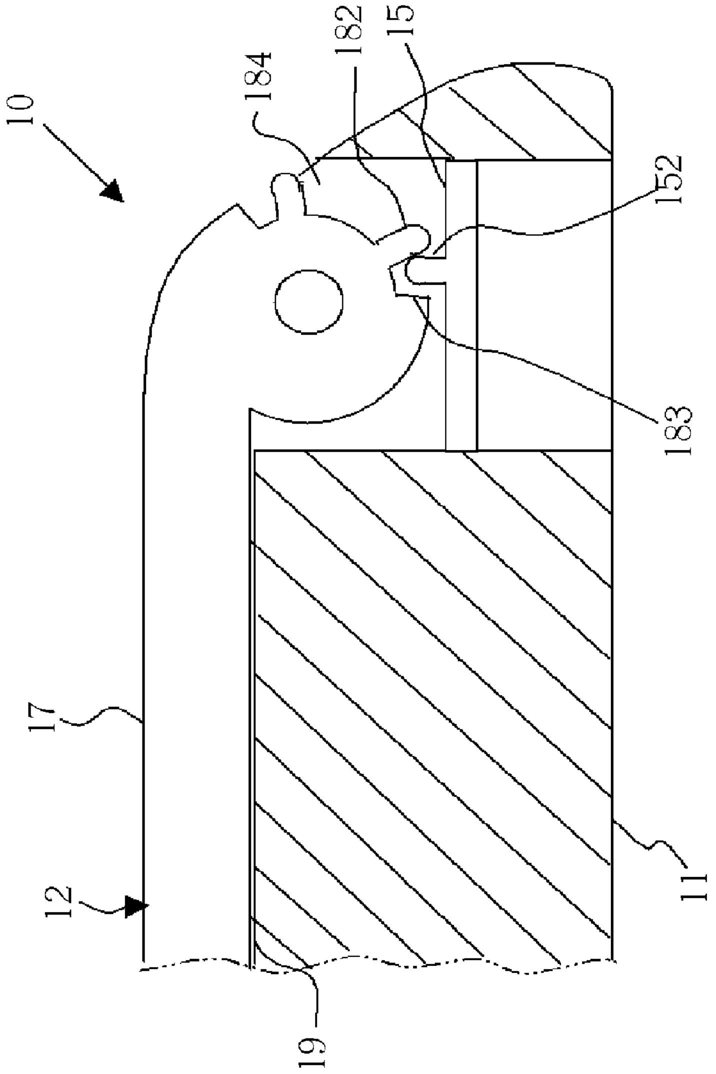
FIG. 5 is a diagram of a second embodiment of the hinge positioning structure according to the present invention.

Although the present invention described above in terms of the preferred embodiment uses a sharp-cornered, rectangular shape for the flanges 182 and the spring strip 152 as an example, the flanges 182 and the spring strip 152 could also have a rounded shape as shown in FIG. 5. The rounded shape reduces rubbing between the flanges 182 and the spring strip 152, while still achieving the effect and goal of the present invention, and also falls within the art of the present invention.

Thus, through the positioning of the stopper 15 and the positioning grooves 183, the stopper 15 of the present invention hinge positioning structure 10 can restrict rotation of the leg 12, providing a strong support, such that the stable positioning of the leg 12 can hold a heavier body. Simultaneously, the flange 182 and the spring strip 152 form a rectangular contact surface which distributes weight from the body, which reduces stress to the flange 182 and the spring strip 152, thereby reducing wear between the components and increasing the life of the product. The hinge positioning structure 10 also can use a smaller leg 12 relative to the weight supported compared to the prior art, while providing a more reliable stand. Finally, the present invention forms the flanges 182 and the positioning grooves 183 directly on the hinge 18, which not only reduces the number and cost of components, but also only requires using screws to fix the stopper 15 to the bottom of the joint groove 13 to complete assembly, which reduces assembly steps and time, thereby also saving cost of manufacturing.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A hinge positioning structure coupled to a body and a leg of a stand comprising:
- a joint groove formed in the body comprising two sides, each side of the joint groove comprising a pivot hole;
- a stopper attached at the bottom of the joint groove having an elastic body comprising a spring strip, the stopper further comprising a baseboard and the spring strip is disposed on the baseboard; and
- a hinge formed in the leg positioned in the joint groove comprising:
  - two sides, each side having a pivot positioned according to the corresponding pivot hole for rotatable insertion into the corresponding pivot hole of the joint groove; and
  - two flanges, each flange parallel to the spring strip and radially protruding a first height sufficient to contact with the spring strip for generating a resistance.

2. The hinge positioning structure of claim 1, wherein the stopper is made of a rubber material.

3. The hinge positioning structure of claim 1, wherein the baseboard comprises:
- two thick sides, each thick side having a screw hole; and
- a protruding center on which the spring strip is disposed.

4. The hinge positioning structure of claim 3, wherein the stopper is attached below the joint groove by screwing a screw into the screw hole of each of the two thick sides and the protruding center is positioned at the bottom of the joint groove.

5. The hinge positioning structure of claim 1, wherein the spring strip is rectangular, positioned along the bottom of the joint groove, and protrudes a second height above the bottom of the joint groove.

6. The hinge positioning structure of claim 1, wherein the stopper has a predetermined range of downward flexibility.

7. The hinge positioning structure of claim 1, wherein the leg comprises a support protruding over the hinge.

8. The hinge positioning structure of claim 1, wherein when one of the two flanges contacts with the spring strip, the leg is relatively closed to the body, and when the other of the two flanges contacts with the spring strip, the leg is relatively open to the body.

9. The hinge positioning structure of claim 8, wherein the hinge further comprises a spacious groove between the two flanges for the spring strip to move without contacting the hinge.

10. The hinge positioning structure of claim 8, wherein the hinge further comprises a spacious groove between inner sides of the two flanges for the spring strip to move without contacting the hinge.

11. The hinge positioning structure of claim 1, wherein the two flanges are rectangular and formed in the direction of an axis of the hinge.

12. The hinge positioning structure of claim 1, wherein the spring strip is not on an axis of the joint groove and forms a rectangular area when contacting with one of the two flanges when the leg is relatively open to the body.

13. The hinge positioning structure of claim 1, wherein the two flanges and the spring strip have rounded edges.

14. The hinge positioning structure of claim 1, wherein the two flanges and the spring strip are cuboids.

15. The hinge positioning structure of claim 1, wherein the hinge further comprises two positioning grooves parallel to each other outside the two flanges.

16. The hinge positioning structure of claim 1, wherein the hinge further comprises two positioning grooves parallel to each other, one of the two positioning grooves being at an outer side of one of the two flanges and the other one of the two positioning grooves being at an outer side of the other one of the two flanges.

17. A hinge positioning structure coupled to a body and a leg of a stand comprising:

a joint groove formed in the body comprising two sides, each side of the joint groove comprising a pivot hole;

a stopper attached at the bottom of the joint groove having an elastic body comprising a spring strip; and a hinge formed in the leg positioned in the joint groove comprising:

two sides, each side having a pivot positioned according to the corresponding pivot hole for rotatable insertion into the corresponding pivot hole of the joint groove;

two flanges, each flange parallel to the spring strip and radially protruding a first height sufficient to contact with the spring strip for generating a resistance; and two positioning grooves parallel to each other outside the two flanges.

18. A hinge positioning structure coupled to a body and a leg of a stand comprising:

a joint groove formed in the body comprising two sides, each side of the joint groove comprising a pivot hole;

a stopper attached at the bottom of the joint groove having an elastic body comprising a spring strip; and a hinge formed in the leg positioned in the joint groove comprising:

two sides, each side having a pivot positioned according to the corresponding pivot hole for rotatable insertion into the corresponding pivot hole of the joint groove;

two flanges, each flange parallel to the spring strip and radially protruding a first height sufficient to contact with the spring strip for generating a resistance; and two positioning grooves parallel to each other, one of the two positioning grooves being at an outer side of one of the two flanges and the other one of the two positioning grooves being at an outer side of the other one of the two flanges.

* * * * *